United States Patent
Dekker et al.

(10) Patent No.: US 8,506,793 B2
(45) Date of Patent: Aug. 13, 2013

(54) CARDIOMYOCYTES-CONTAINING DEVICE AND METHOD FOR MANUFACTURING AND USING THE SAME

(75) Inventors: Ronald Dekker, Eindhoven (NL); Anja Van De Stolpe, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 28 days.

(21) Appl. No.: 13/147,607

(22) PCT Filed: Feb. 2, 2010

(86) PCT No.: PCT/IB2010/050537
§ 371 (c)(1),
(2), (4) Date: Dec. 8, 2011

(87) PCT Pub. No.: WO2010/089718
PCT Pub. Date: Aug. 12, 2010

(65) Prior Publication Data
US 2012/0094323 A1 Apr. 19, 2012

(30) Foreign Application Priority Data
Feb. 9, 2009 (EP) .................................... 09152378

(51) Int. Cl.
*G01N 27/327* (2006.01)
(52) U.S. Cl.
USPC ...................................... 205/792; 204/403.01
(58) Field of Classification Search
USPC ............................... 205/775, 792; 204/403.01
See application file for complete search history.

(56) References Cited

U.S. PATENT DOCUMENTS

| 6,730,199 B1 * | 5/2004 | Hanni et al. ............. 204/403.02 |
| 8,202,720 B2 * | 6/2012 | Yasuda et al. ............ 435/288.7 |
| 2004/0010819 A1 | 1/2004 | DeBonte et al. |
| 2004/0106095 A1 | 6/2004 | Thomson et al. |

(Continued)

FOREIGN PATENT DOCUMENTS

| WO | WO2004061954 | 7/2004 |
| WO | WO2005098425 | 10/2005 |
| WO | WO2008045506 | 4/2008 |

OTHER PUBLICATIONS

Egert et al., "Heart on a Chip—Extracellular Multielectrode Recordings from Cardiac Myocytes in Vitro," Chapter 3.10, pp. 432-453, from Practical Methods in Cardiovascular Research, published 2005 by Springer-Verlag Berlin Heidelberg.*

(Continued)

*Primary Examiner* — Alex Noguerola

(57) ABSTRACT

Disclosed is a device for determining the cardiotoxicity of a chemical compound, comprising a substrate (10) carrying a deformable stack (34), said stack being partially detached from the substrate by a cavity (32) allowing an out-of-plane deformation of the stack, said stack comprising a first deformable layer (16), a second deformable layer (20) and a multi-electrode structure (18) sandwiched between the first and second deformable layers, the second deformable layer carrying a pattern of cardiomyocytes (28) adhered thereto; and a liquid container (26) mounted on the substrate for exposing the cardiomyocytes to the chemical compound. A method of manufacturing such a device is also disclosed. The present invention further relates to the use of the device for drug target discovery and/or drug development and a method for developing a disease model for a disease that is caused by or modified by stretching of cells, in particular a cardiac disease model.

17 Claims, 13 Drawing Sheets

(56) References Cited

U.S. PATENT DOCUMENTS

Figure 1:
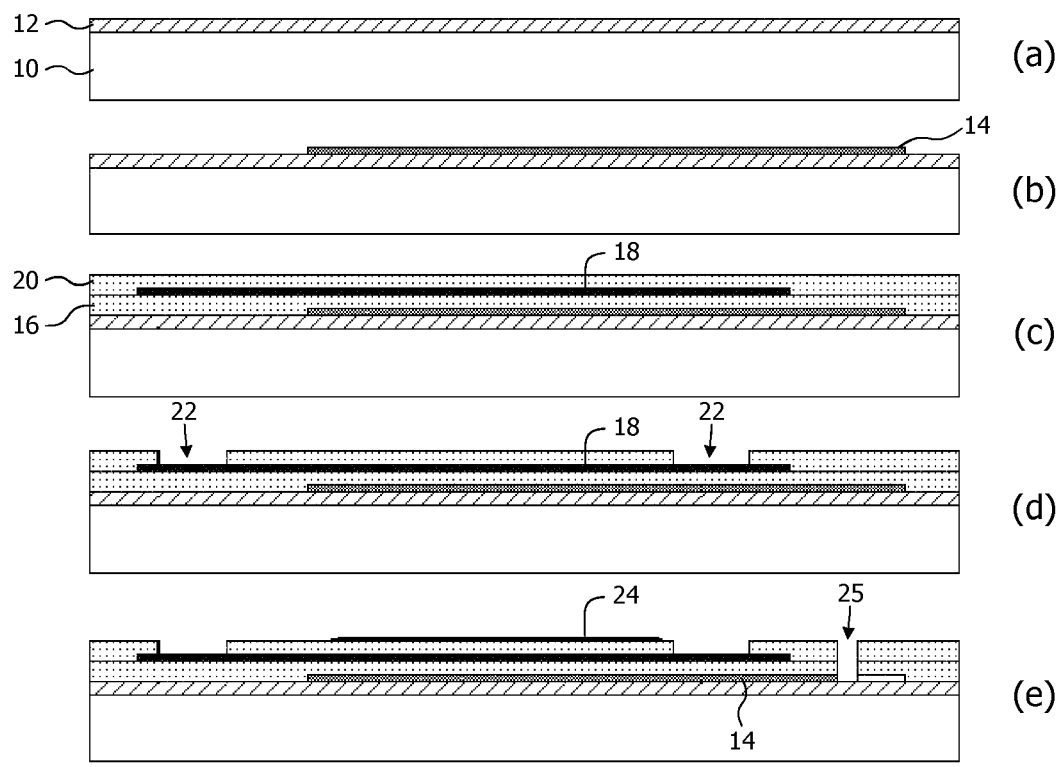
Figure 1:
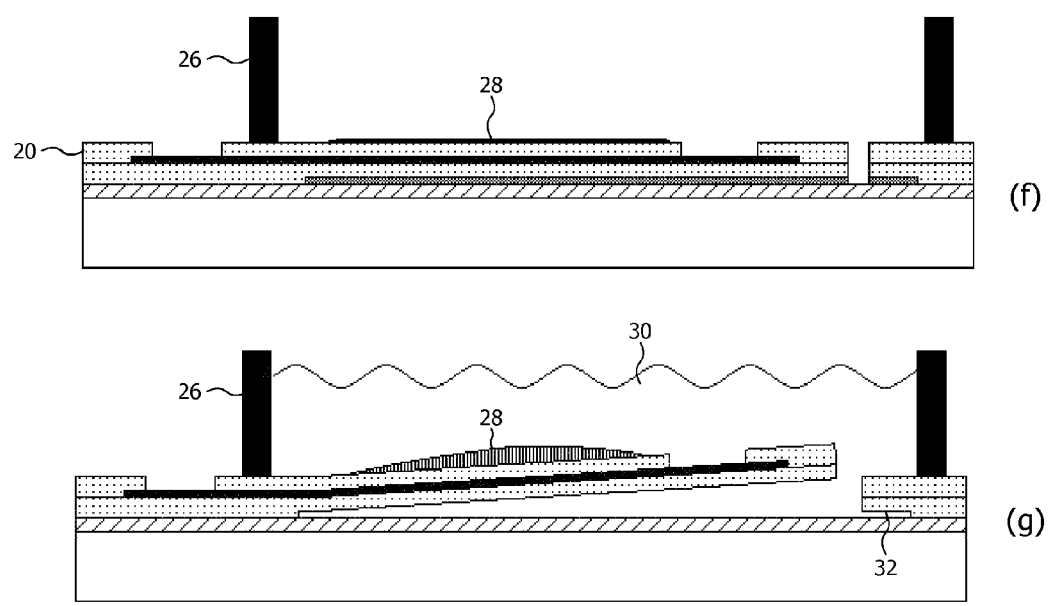

| | | |
|---|---|---|
| 2004/0243204 A1 | 12/2004 | Maghribi et al. |
| 2006/0073539 A1 | 4/2006 | Wikswo et al. |
| 2011/0039294 A1* | 2/2011 | Wang et al. .................. 435/29 |

OTHER PUBLICATIONS

R. Dekker et al., "Moore With Less Silicon: How the Silicon Substrate Slowly Comes Alive", Maxwell 1 1.2, Mar. 2008, pp. 9-11.

J. Yu, et al., "Pluripotent Stem Cell Lines", Genes & Development 22:1987-1997, 2008 by Cold Spring Harbor Laboratory Press, pp. 1987-1997.

A. Werdich, et al., "A Microfluidic Device to Confine a Single Cardiac Myocyte in a Sub-Nanoliter Volume on Planar Microelectrodes for Extracellular Potential Recordings", Miniatureisation for chemistry, Biology & Bioengineering, Lab Chip 2004, 4, pp. 357-362.

H. Yu, et al., "A novel Design of Multifunctional Integrated Cell-Based Biosensors for Simultaneously Detecting Cell Acidification and Extracellular Potential", Biosensors and Bioelectronics 24 (2009), pp. 1462-1468.

J. Deutsch, et al., "Fabrication of Microtextured Membranes for Cardiac Myocyte Attachment and Orientation", J. Biomed. Mater. Res., vol. 53, 2000, pp. 267-275.

J. Park, et al., "Real-Time Measurement of the Contractile Forces of Self-Organized Cardiomyocytes on Hybrid Biopolymer Microcantilevers", Anal. Chem., vol. 77, 2005, pp. 6571-6580.

M.C. Heidkamp, et al., "Calcium Not Strain Regulates Localization of A-Myosin Heavy Chain MRNA in Oriented Cardiac Myocytes", Cell Tissue Res., vol. 305, 2001, pp. 121-127.

S.S. Lateef, et al., "GRGDSP Peptide-Bound Silicon Membranes Withstand Mechanical Flexing in Vitro and Display Enhanced Fibroblast Adhesion", Biomaterials, vol. 23, No. 15, Aug. 2002, pp. 3159-3168.

Z. Feng, et al., "Technological Developments in Japan—An Electro-Tensile Cardiomyocytes—A Bioreactor System That Simulates the myocardium's Electrical and Mechanical Response in Vivo", IEEE Engineering in Medicine and biology Magazine, vol. 24, No. 4, Jul. 2005, pp. 73-79.

Q. Liu, et al., "Detection of Heavy Metal Toxicity Using Cardiac Cell-Based Biosensor", Biosensors & Bioelectronics, vol. 22, No. 12, Jun. 15, 2007, pp. 3224-3229.

* cited by examiner

CARDIOMYOCYTES-CONTAINING DEVICE AND METHOD FOR MANUFACTURING AND USING THE SAME

FIELD OF THE INVENTION

The present invention relates to a device for determining cardiotoxicity of a chemical compound.

The present invention further relates to a method of manufacturing such a device.

The present invention yet further relates to a method of determining the cardiotoxicity of a chemical compound using such a device.

The present invention further relates to the use of the device for drug target discovery and/or drug development.

The present invention further relates to a method for developing a disease model for a disease that is caused by or modified by stretching of cells, in particular a cardiac disease model.

BACKGROUND OF THE INVENTION

Many drugs have cardiotoxic side effects, e.g. arrhythmias or negative effects on the contractive capacity of the heart muscle. Over the last years it has become evident that a common side-effect of a number of drugs is a prolonging effect on the QT interval in the cardiac cycle, which is an important cause of drug-induced life threatening arrhythmias. For instance, during the past years, the development of several drugs has been aborted in late phases of preclinical testing or clinical trials, and even post-marketing due to undesirable effects on the QT interval of the surface electrocardiogram (ECG). A prolongation of this interval to more than 440 to 460 msec may allow life threatening arrhythmias, e.g. torsade de pointes (TdP), to occur and has been associated with a wide variety of drugs.

This was acknowledged in 1998 when the Food and Drug Administration (FDA) defined prolongation of the QT interval as a major drug safety issue. Subsequently, identification of QT prolongation and clinical torsade de pointes has led to the removal of several drugs from the market in the United States, including terfenadine, astemizole, thioridazine, and grepafloxacin, while many others have been required by the FDA to carry additional safety labeling warning of the potential risk. Currently, assessing risk for delayed ventricular repolarization and QT interval prolongation is part of the standard non-clinical evaluation of NCE's as adopted by the FDA and EMEA for all drugs in development.

Unfortunately, currently available preclinical in-vitro cell-based model systems to test for cardiotoxicity are inadequate for detecting the majority of these side-effects, while predictive in-vivo animal studies are very expensive, as well as ethically challenged. In addition, cardiotoxicity results obtained from animal studies cannot be easily extrapolated to humans.

The testing process is further complicated by the fact that these cardiotoxic effects of drugs may only become apparent during actual cardiac muscle stretching and contraction as occurs in vivo in the beating heart, especially during (strenuous) physical exercise; and in cardiac diseases, for example diseases associated with cardiac overload, e.g. heart failure, and diseases characterized by inflammation, like during influenza infections. Currently no testing model systems exist that simulate a normal beating heart, in either a physiological situation, i.e. a stretch-contraction cycle, or a pathophysiological situation, such as excessive stretch/contraction against increased pressure, associated with cardiac failure. Moreover, different drugs can have different negative effects on the heart function.

Some human cell-based model systems are available for cardiotoxicity testing. These model systems typically may consist of cardiomyocytes, either animal or human, and either primary cardiomyocytes or stem cell-derived cardiomyocytes on standard multi-electrode arrays (MEA), as disclosed in "Pluripotent stem cell lines" J. Yu and J. A. Thomson, Genes Dev. 2008, 22, p. 1987-1997. However the usefulness of these systems is constrained by the fact that these are static model systems not taking into account the dynamics of the beating heart.

In 'An Electro-Tensile Bioreactor for 3-D Culturing of Cardiomyocytes' by Zhonggang Feng et al. in IEEE Engineering in Medicine and Biology Magazine, July/August 2005, pages 73-79, a bioreactor is disclosed which allows for the in-plane stretching of a cardiomyocyte-containing gel layer disposed on a stretchable silicone plate to simulate the mechanical and electrical response of the myocardium in vivo. A drawback of this device is that it is quite complex and not particularly suitable for cardiotoxicity testing due to the fact that the cardiomyocytes are embedded in a gel.

SUMMARY OF THE INVENTION

The present invention seeks to provide an improved device for determining the cardiotoxicity of a chemical compound.

The present invention further seeks to provide a method of manufacturing such an improved device.

The present invention yet further seeks to provide a method of determining the cardiotoxicity of a chemical compound using such an improved device.

The present invention further seeks to provide a method of developing (cardiac) disease models using such an improved device.

According to a first aspect of the present invention, there is provided a device for determining the cardiotoxicity of a chemical compound, comprising a substrate carrying a deformable stack, said stack being partially detached from the substrate by a cavity allowing an out-of-plane deformation of the stack, said stack comprising a first deformable layer, a second deformable layer and a multi-electrode structure sandwiched between the first and second deformable layers, the second deformable layer carrying a pattern of cardiomyocytes adhered thereto and a liquid container mounted on the substrate for exposing the cardiomyocytes to the chemical compound.

The presence of the cavity ensures that at least the central region of the first deformable layer, e.g. an elastomer layer, is not attached to the substrate, such that this region can move freely, e.g. as triggered by a contraction of the cardiomyocytes. The provision of the cavity ensures that the cardiomyocyte contraction induced movement can be facilitated in a relatively simple manner, thereby reducing the cost of the device of the present invention compared to the devices available in the art.

In an embodiment, one end of the deformable stack is detached from the substrate to facilitate the out-of-plane deformation, e.g. curling, upon contraction of the cardiomyocytes. This has the advantage that the cardiomyocyte contraction can be monitored electrically through the electrode arrangement as well as optically, through the amount of curling. In addition, the curling principle ensures that the intrinsic resistance of the stack to the deformation forces of the contracting cardiomyocytes is low, such that the contraction is not significantly hampered by this resistance.

In a preferred embodiment, the substrate comprises the cavity, the stack extending over the cavity, wherein opposite ends of the stack are attached to the substrate, thereby facilitating the out-of-plane deformation of the stack by an externally applied force. This has the advantage that the device can also be used to train immature cardiomyocyte cells by stretching the cells during the out-of-plane deformation of the deformable stack, such that the differentiation and maturation process of the live cardiomyocyte cells is accelerated. In addition, contraction of the cardiomyocytes is still facilitated due to the fact that the stretchable nature of the stack allows for an in-plane cardiomyocyte-induced stretching of the deformable layers, such that both cardiomyocyte stretching and contraction during diastole and systole respectively can be simulated with this device in a quantitative manner at the appropriate stretch-contraction cycle frequency. This may stimulate further differentiation and maturation of stem cell-derived cardiomyocytes.

The device may comprise an inlet for filling the cavity with a fluid. In an embodiment, the fluid is a gas (e.g. air), such that the out-of-plane deformation of the stack may be controlled by controlling the gas (e.g. air) pressure inside the cavity, thereby simulating the beating of the heart. This has the advantage that no contact with the stack is required to invoke the out-of-plane deformation, thus reducing the risk of contamination or damage to the cardiomyocytes. In an alternative embodiment, the fluid is a liquid, and the stack comprises the inlet. The provision of the inlet in the stack further facilitates the stretching of the stack during a contraction cycle of the cardiomyocytes, thereby for instance enabling the use of a linear electrode array. In this embodiment, any fluid placed in the container will envelop both surfaces of the stack such that the load of the fluid on the stack will effectively be zero. In this case, the out-of-plane deformation of the stack may be mechanically invoked. Out-of-plane deformations of the stack of 100% and more can be obtained.

In an embodiment, the stack is corrugated to make it deformable. The corrugations further reduce the intrinsic resistance of the stack to the contraction forces of the cardiomyocytes, thereby improving the cardiomyocyte contraction behavior of the device.

In accordance with another aspect of the present invention, a method of manufacturing a device of the present invention is provided. This method comprises growing an oxide layer of the substrate; depositing the first deformable layer over the oxide layer; depositing and patterning a conductive layer over the first deformable layer, thereby forming the multi-electrode structure, depositing a second deformable layer over the first deformable layer, patterning the second deformable layer to provide access to the multi-electrode structure, depositing an adhesive pattern over the patterned second deformable layer, adhering cardiomyocytes to the adhesive pattern, adhering the liquid container to the second deformable layer and forming the cavity underneath the first deformable layer.

This method has the advantage that the device of the present invention can be formed at low cost, thereby making the method attractive for large scale production purposes.

The order in which the steps of this method are performed may be altered without departing from the scope of the present invention. For instance, the steps of depositing an adhesive pattern over the patterned second deformable layer and adhering cardiomyocytes to the adhesive pattern may be performed after forming the cavity underneath the first deformable layer. This has the advantage that the cardiomyocytes can be applied to the second deformable layer immediately prior to use, thereby ensuring that the cardiomyocytes are in a good condition during use.

In an embodiment, forming said cavity comprises depositing a sacrificial layer over the oxide layer prior to the deposition of the first deformable layer, said sacrificial layer defining the cavity volume and removing the sacrificial layer after the deposition of the second deformable layer. This has the advantage that the stack may be formed over the sacrificial layer rather than over the cavity, thereby simplifying the manufacturing process because no complex steps are required to form the stack over a void.

In an alternative embodiment, forming said cavity comprises applying a mask on the backside of the substrate; patterning said mask to define the cavity area; etching the backside of the substrate to expose the first deformable layer; and removing the patterned mask from the backside of the substrate. This has the advantage that the stack may be formed over the substrate rather than over the cavity, thereby simplifying the manufacturing process as previously explained.

Advantageously, the method further comprises forming a corrugated pattern in the substrate prior to forming the oxide layer. This has the advantage that the deformability may be achieved by the flexibility of the corrugations, which aids the contraction cycle of the cardiomyocytes as previously explained.

In an embodiment, said corrugated pattern is formed through milling. In an alternative embodiment, forming said corrugated pattern comprises depositing a silicon oxide layer over the substrate; depositing a silicon nitride layer over the silicon oxide layer; patterning the silicon oxide and silicon nitride layer, thereby exposing selected parts of the substrate; exposing said selected parts to a series of etching steps to form said corrugated pattern; and removing the silicon oxide and silicon nitride layer. This has the advantage that the corrugated pattern may be formed using readily available semiconductor processing techniques, thereby limiting the complexity and cost of the device manufacture.

Alternatively, said corrugated pattern may be formed by a LOCOS oxidation step followed by an etching step in which the LOCOS oxide is removed. This also has the advantage that the corrugated pattern may be formed using readily available semiconductor processing techniques, thereby limiting the complexity and cost of the device manufacture.

According to yet a further aspect of the present invention there is provided a method of determining the cardiotoxicity of a chemical compound, comprising providing the device according to an embodiment of the present invention; filling the container with a medium comprising the chemical compound to expose the cardiomyocytes to said compound; and measuring the response of the cardiomyocytes to said exposure.

The use of the device of the present invention in such a method provides an improvement in the accuracy of the cardiotoxicity determination of chemical compounds such as trial drugs.

The present invention further relates to a method for developing a disease model for a disease that is caused by or modified by stretching of cells, the method comprising the steps of:

Attaching at least one cell to an adhesive surface pattern

Stretching the at least one cell by an externally applied force

Measuring an action potential of the at least one cell electrically and/or optically, the action potential being monitored and/or interpreted over time.

The method is in particular suitable for establishing a cardiac disease model (among other disease models where cell stretch and measuring ion channel activity and electric potential is relevant). It is a big advantage that heart cell toxicity can be measured under conditions simulating increased heart load (stress) during physical exercise or other conditions associated with increased cardiac output. It is a further advantage that heart cell toxicity can be determined under conditions of heart disease, like cardiac failure, cardiomyopathy etc. The effect of a specific genetic variable on cardiotoxicity can be taken into account in the method.

In an advantageous method, the stretching of the at least one cell may be in-plane and/or out-of plane with respect to the adhesive surface pattern. The percentage of cell stretching in-plane is larger than 30% and the stretching time is varied.

Preferably, during the measurement chemical or biological compounds are added.

The use of the device according to the invention allows the development of accurate heart disease models for drug discovery and development, also on a personalized basis, taking human genetic variables into account.

BRIEF DESCRIPTION OF THE EMBODIMENTS

Figure 2:
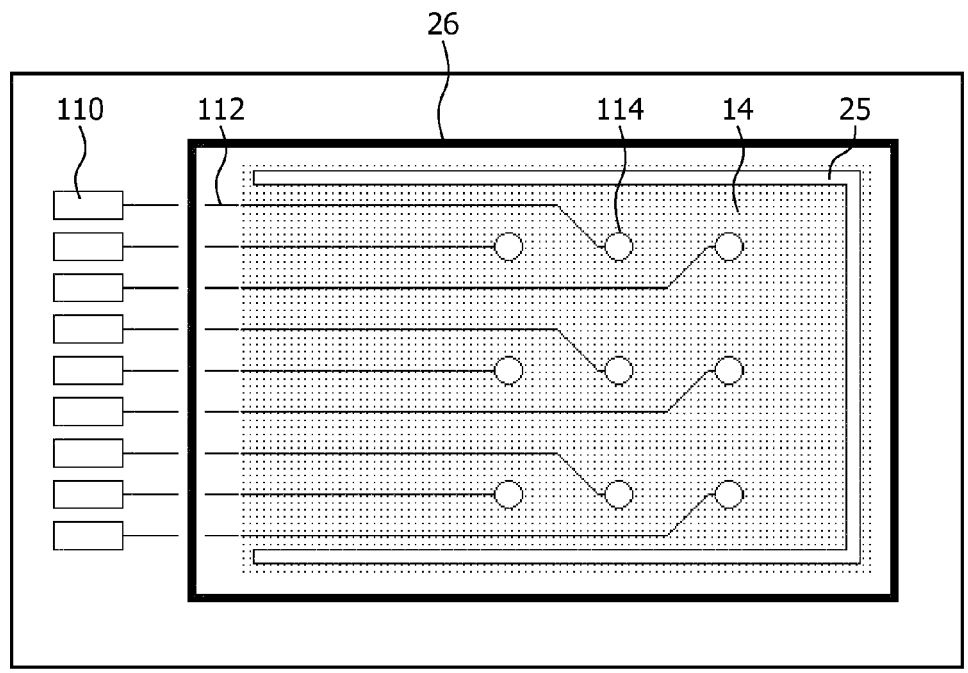
Figure 3:
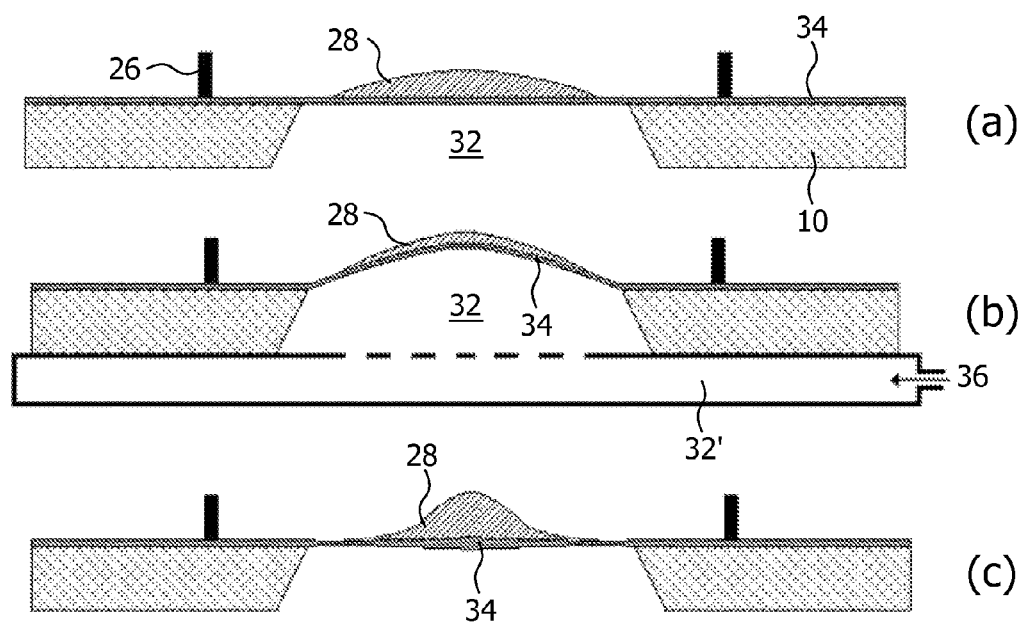
Figure 4:
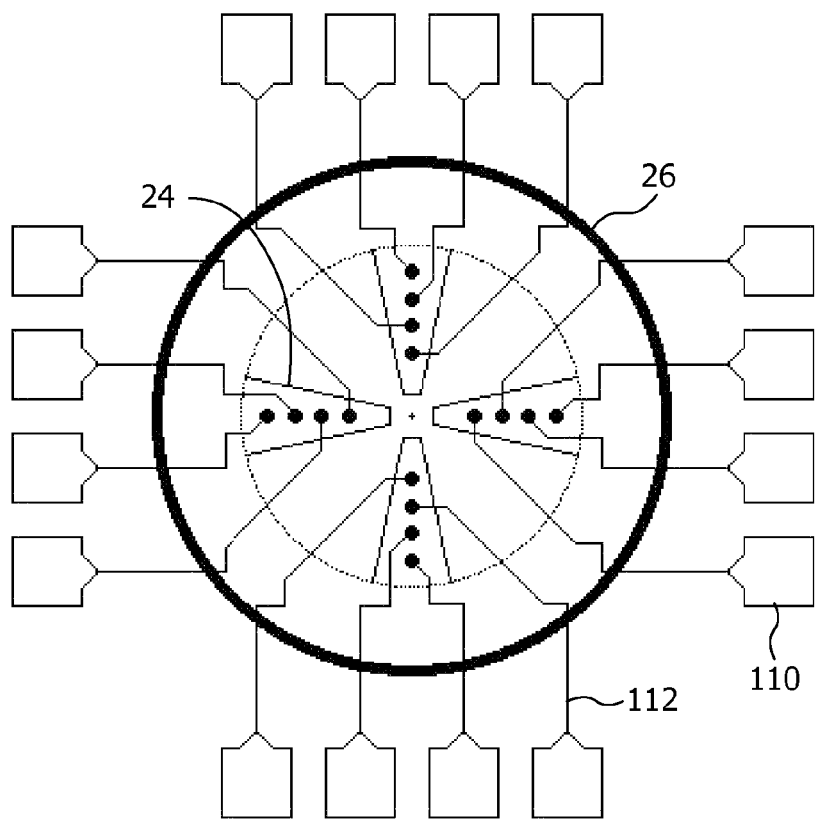
Figure 5:
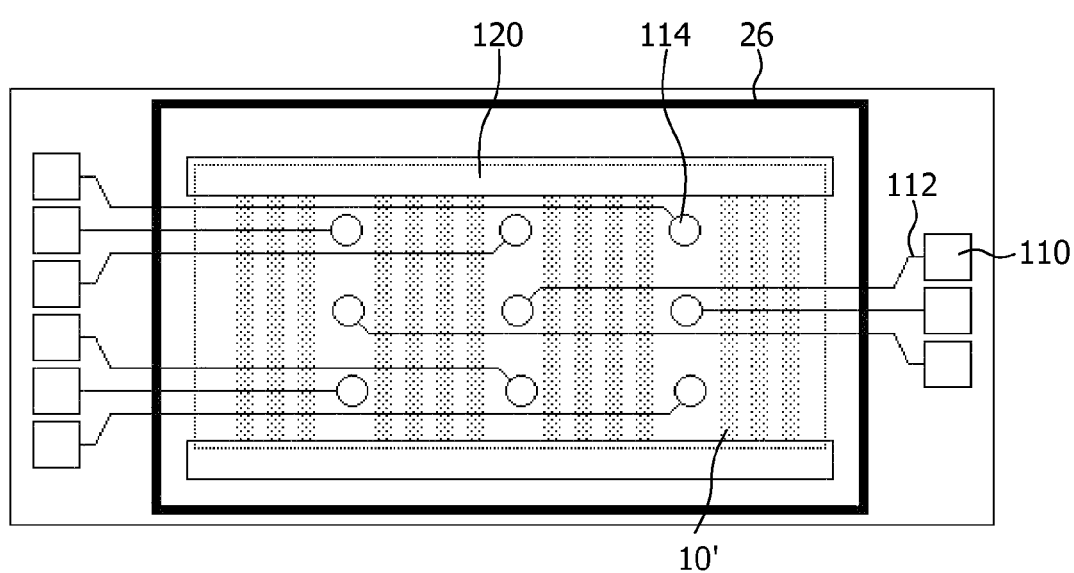
Figure 6:
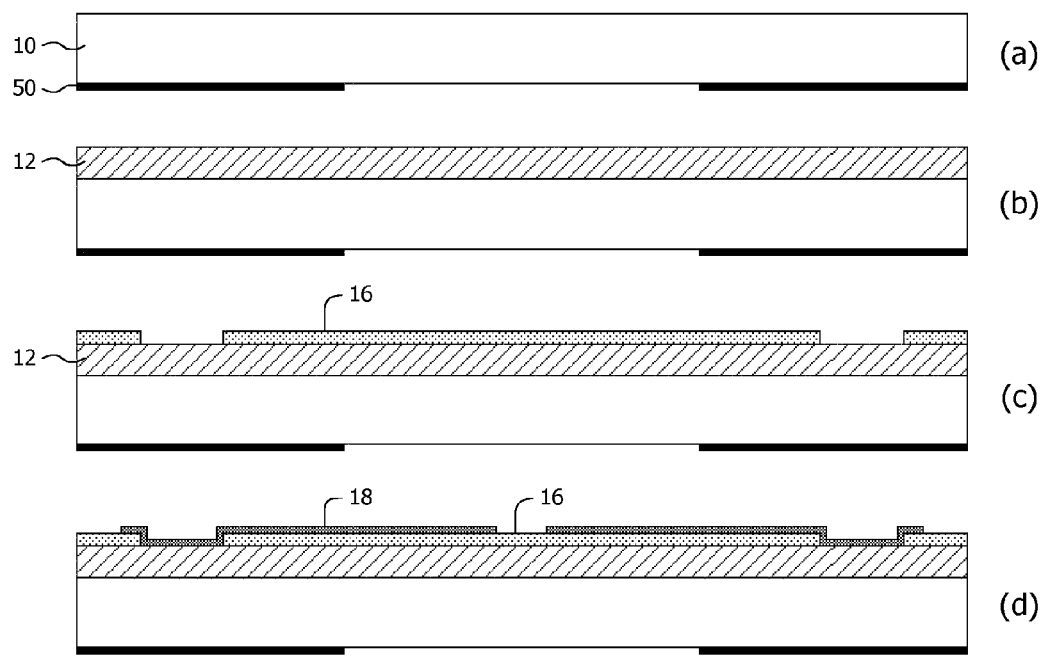
Figure 6:
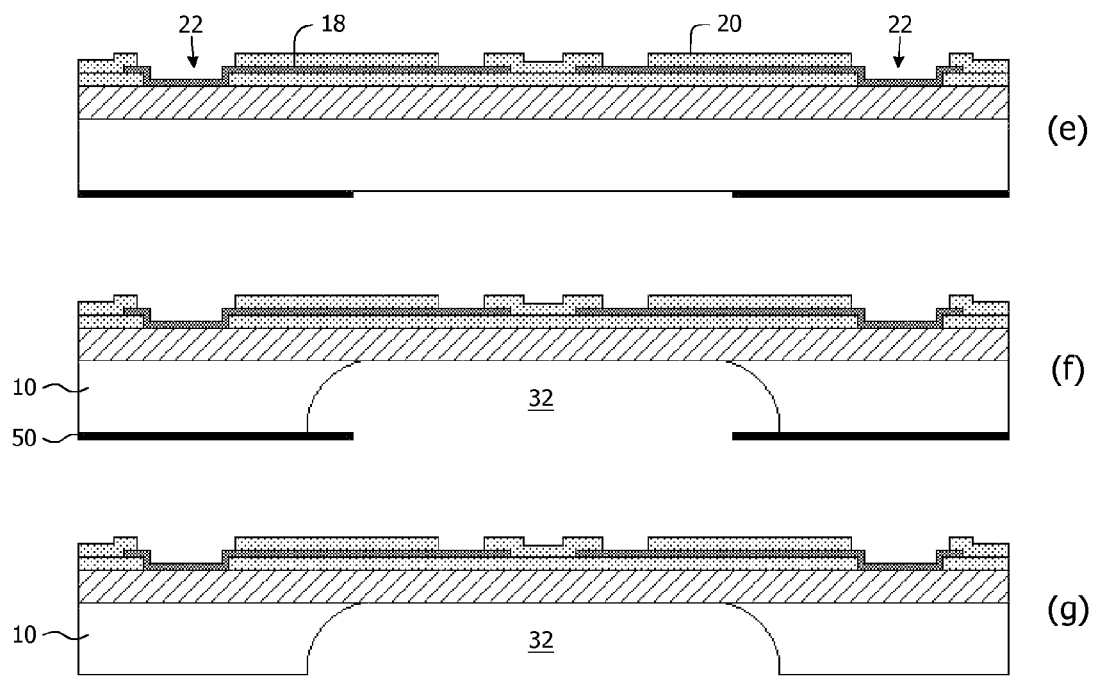
Figure 6:
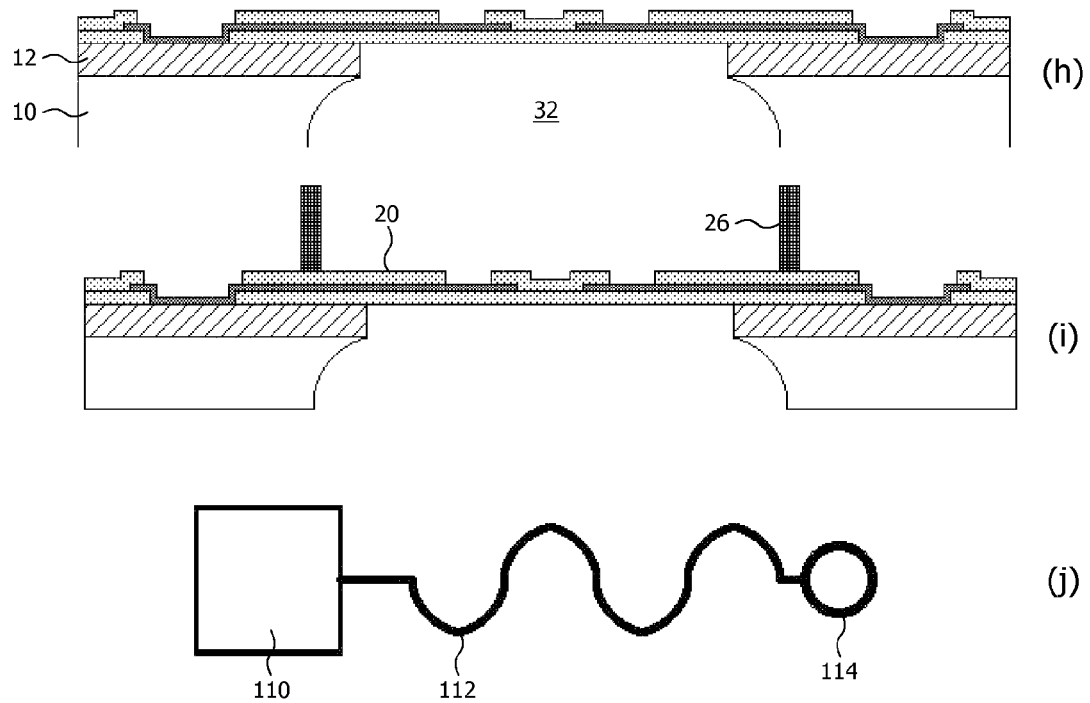
Figure 7:
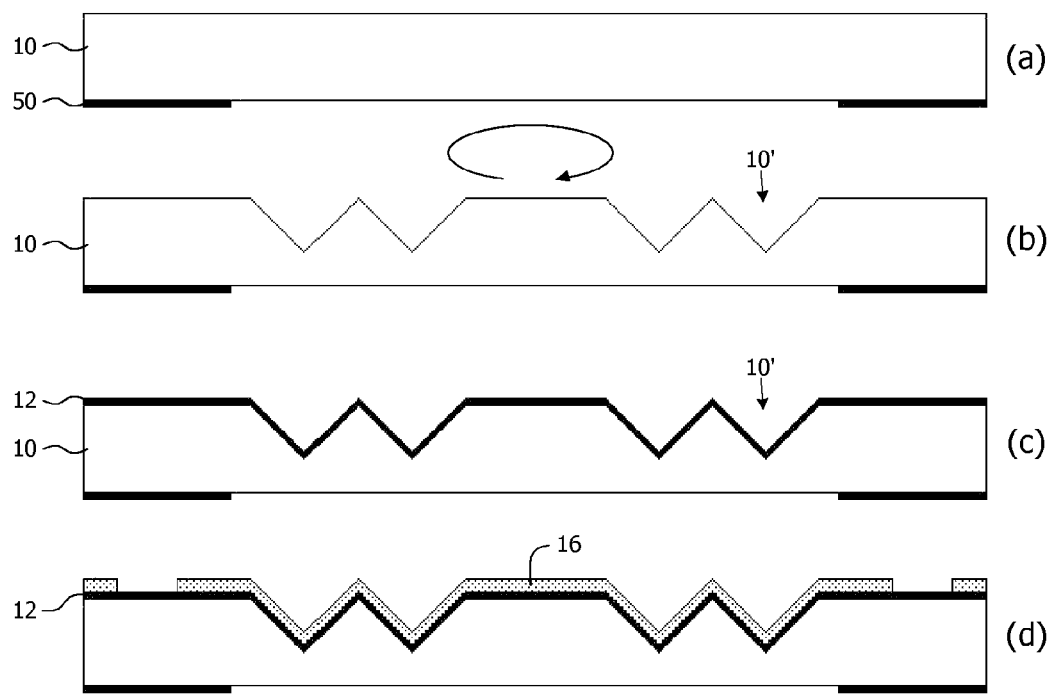
Figure 7:
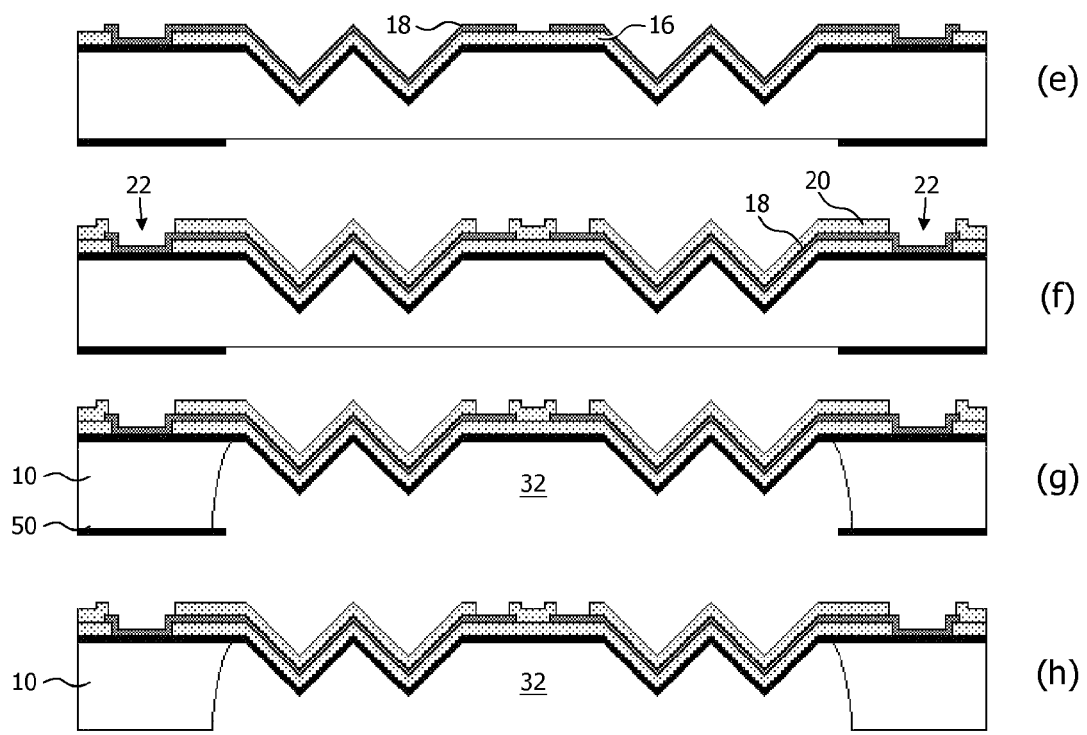
Figure 7:
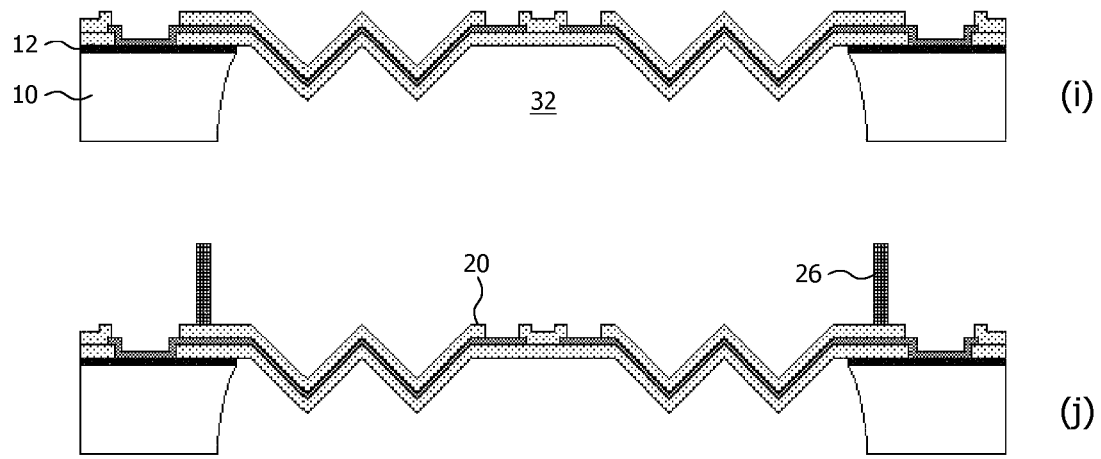
Figure 8:
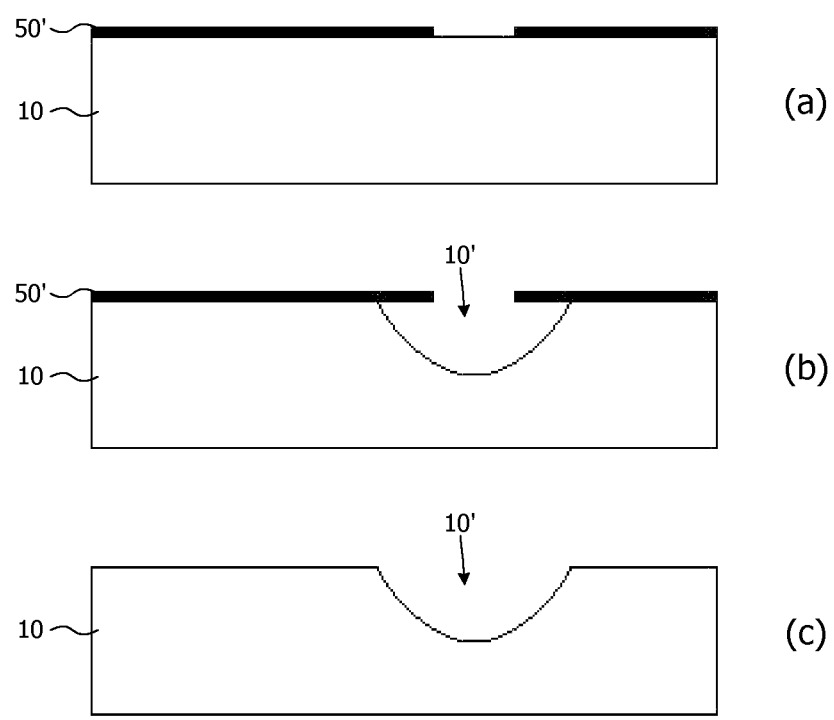
Figure 9:
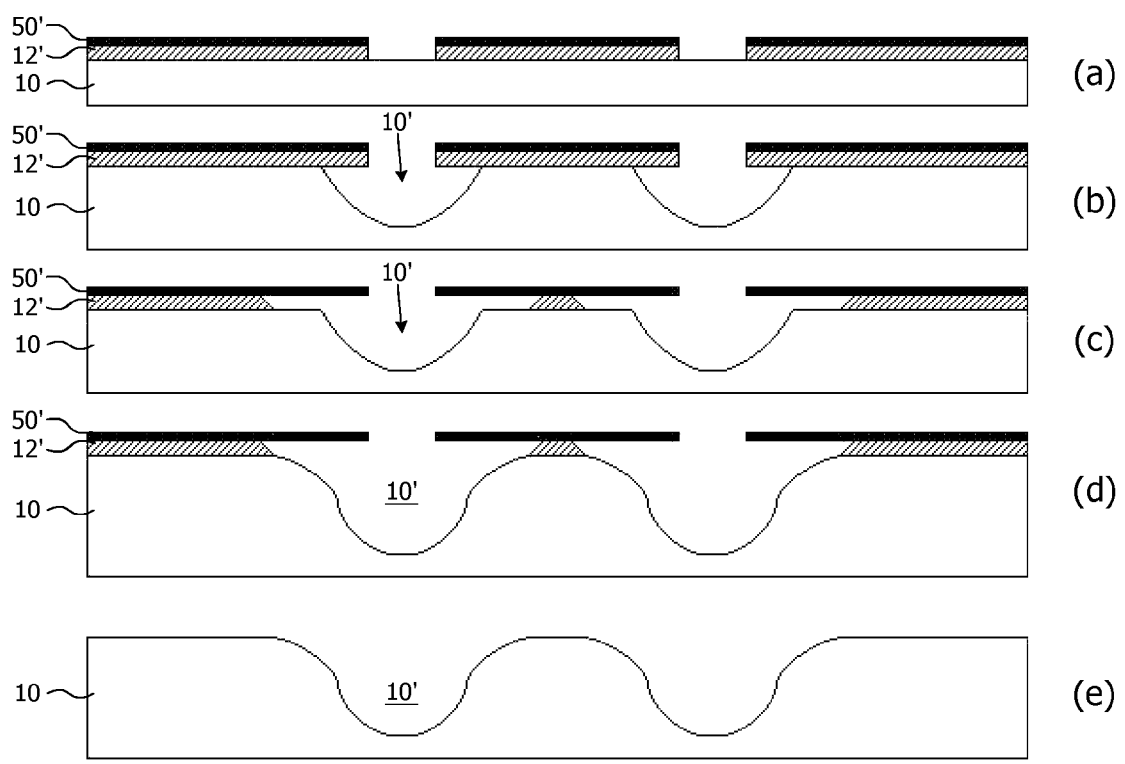
Figure 10:
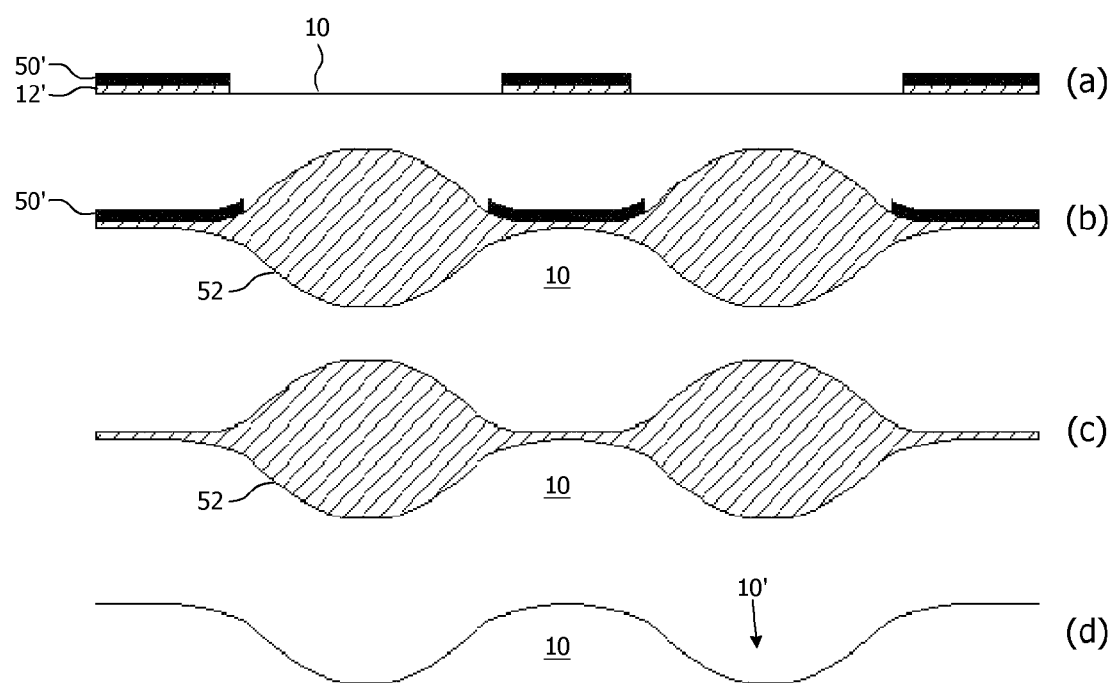

Embodiments of the invention are described in more detail and by way of non-limiting examples with reference to the accompanying drawings, wherein FIG. 1 (a)-(g) schematically depicts a method of manufacturing a device for determining the cardiotoxicity of a chemical compound in accordance with an embodiment of the present invention;

FIG. 2 schematically depicts a top view of the device for determining the cardiotoxicity of a chemical compound as obtained by the method of FIG. 1;

FIG. 3 (a)-(c) schematically depicts a device for determining the cardiotoxicity of a chemical compound in accordance with another embodiment of the present invention;

FIG. 4 schematically depicts an example electrode arrangement for a device for determining the cardiotoxicity of a chemical compound according to the present invention;

FIG. 5 schematically depicts an alternative example electrode arrangement for a device for determining the cardiotoxicity of a chemical compound according to the present invention;

FIG. 6 (a)-(j) schematically depicts a method of manufacturing a device for determining the cardiotoxicity of a chemical compound in accordance with an alternative embodiment of the present invention;

FIG. 7 (a)-(h) schematically depicts a method of manufacturing a device for determining the cardiotoxicity of a chemical compound in accordance with yet another embodiment of the present invention; and FIGS. 8-10 show alternatives for a part of the method of FIG. 7.

DETAILED DESCRIPTION OF THE DRAWINGS

It should be understood that the Figures are merely schematic and are not drawn to scale. It should also be understood that the same reference numerals are used throughout the Figures to indicate the same or similar parts.

The device for determining the cardiotoxicity of a chemical compound of the present invention is based on the following general structural principle. An elastomer-based stack is mounted over a cavity in a substrate. This cavity effectively detaches a part of the elastomer-based stack from the substrate, such that the elastomeric nature of this part is facilitated to move out of the plane of the surface of the substrate. Several embodiments of such a device are contemplated, as will be discussed in more detail below.

In FIG. 1, a method of manufacturing a first embodiment of the device of the present invention is depicted. In a first step (a), a substrate 10, e.g. a silicon wafer, a glass substrate or any other suitable substrate material is provided and a dielectric layer 12 such as a silicon oxide layer is formed over a surface of the substrate 10. The formation of a dielectric layer 12 on a substrate 10 is well-known to the person skilled in the art and will not be further explained for reasons of brevity only.

In a next step (b), a sacrificial material 14 is deposited over the dielectric layer 12 and subsequently patterned. The patterned sacrificial material 14 defines the cavity to be formed. Any suitable sacrificial material, such as a soluble or decomposable polymer may be used. A suitable non-limiting example of such a polymer is poly-N-isopropylacrylamide (PIPAAm).

In step (c), an elastomer-based stack is formed over the patterned sacrificial material 14 and the dielectric layer 12. This stack comprises a first elastomer layer 16, a patterned metal layer 18 formed on the first elastomer layer 16 and a second elastomer layer 20 covering the patterned conductive layer 18 such that the conductive layer is sandwiched between the first elastomer layer 16 and the second elastomer layer 20.

Any suitable elastomer layer may be used. In an embodiment, the first elastomer layer 16 is a polydimethylsiloxane (PDMS) layer, which may be applied by means of spin-coating. Any suitable conductive material, e.g. a metal, may be applied on this layer. For instance, a TiN layer or a Ti/Au layer stack may be deposited over the PDMS layer 16 and subsequently patterned. A second PDMS layer 20 may be spin-coated over the patterned conductive layer 18. The patterned conductive layer typically comprises electrodes, bond pads and connections between the bond pads and electrodes. This will be explained in more detail later.

In step (d), contacts 22 to the electrodes and bond pads in the patterned conductive layer 18 are formed in any suitable manner, e.g. by RIE etching. This is followed by the application of a fixating layer 24 to an area of the second elastomer layer 20 over the electrodes in the patterned conductive layer 18 for fixating the live cardiomyocyte cells to the elastomer-based stack, as shown in step (e). The live cardiomyocyte cells may be any suitable type of cardiomyocytes, such as human or animal primary cells, or human stem cell-derived cells.

An example of a suitable material for the fixating layer 24 is fibronectin, which may be applied by stamp-, screen- or ink-jet printing. The cardiomyocytes may subsequently be bonded to this layer. It will be obvious to the skilled person that fibronectin is a non-limiting example of such a fixating layer, and that other suitable adhesive materials may also be considered.

The size of the elastomer-based stack defining the electrode array foil may be determined by (laser) cutting the stack and sacrificial material layers, thereby providing a cut 25, which also acts as an access to the sacrificial material 14. This step is followed by step (f), in which a liquid container 25 is attached to the device in any suitable manner, e.g. by gluing. Finally, the sacrificial material is removed, as shown in step (f). For instance, in case of the sacrificial material being PIPMAAm, this may be removed by dissolving this layer in Tyrode's solution. This has the advantage that the cardiomyocytes may already be present on the fixating layer 24 due to the isotonic nature of Tyrode's solution. In case of a thermally decomposable material, the removal may be achieved by exposing the device to a temperature above the decomposition temperature of the material. In this embodiment, care has to be taken that a material is chosen that decomposes at a temperature low enough to avoid damage to other layers of the device. To this end, both the fixating layer 24 and cardiomyocytes may be applied to the elastomer-based stack after removal of the thermally decomposable material.

In an embodiment, the elastomer-based stack or foil has a thickness in the range of 3-10 micron. In this range, the elastomer-based stack or foil has a particularly good flexibility.

FIG. 1(g) demonstrates the device according to this embodiment of the invention in operation. The liquid container 26 is filled with a solution 30 comprising the chemical compound to be tested on the cardiomyocytes 28. The solution 30 embedding the cardiomyocytes may contain both the test compound in various concentrations as well as varying concentrations of molecules, e.g. electrolytes such as potassium, sodium, calcium, glucose, oxygen, $CO_2$, required to simulate different (patho)physiological situations in vivo, such as conditions induced by strenuous exercise.

The cavity 32 under the elastomer-based stack carrying the cardiomyocytes 28 allows for the out-of-plane curling of this stack as triggered by the contraction of the cardiomyocytes 28. The field potential recorded by the electrodes in the patterned metal layer 18 during the stretch-contraction cycle of the cardiomyocytes 28 can be used to determine the effect of the chemical compound on the conductivity in the ion channels of the cardiomyocytes 28.

In the context of the present invention, it should be understood that the phrase 'chemical compound' is not intended to be limited to compounds intended for use as a pharmaceutical or to single compounds only. In general, any substance, such as compound mixtures, emulsions and solutions comprising one or more compounds may be tested using the device of the present invention.

A top view of the electrode array of the device shown in FIG. 1(f) prior to the removal of the sacrificial layer 14 is shown in FIG. 2. The patterned conductive layer 18 comprises a plurality of bond pads 110 that are connected to respective electrodes 114 through conductive connectors 112. The liquid container 26 is shaped such that it envelopes all the electrodes 114. The cut 25 is also shown, which defines the portion of the stack that can curl up as previously explained. The cut 25 extends though the underlying sacrificial layer 14. This facilitates the removal of this layer, as previously explained. The fixating layer 24, e.g. the protein fibronectin, is preferably patterned in the form of stripes (not shown) in the length direction of the stack. This maximizes the curling of the stack upon contraction of the cardiomyocytes 28 adhered to these stripes.

In an alternative embodiment of the present invention, the cavity 32 is formed in the substrate 10, with the deformable stack covering an access to the cavity 32 such that a change in pressure on the elastomer-based stack will allow for a deformation of the stack into or away from the cavity 32. In a first embodiment, an elastomer-based stack may be used, the operating principle of which is demonstrated in FIG. 3. As shown in FIG. 3(a), the substrate 10 comprises a cavity 32 extending through the substrate, which is covered by the elastomer-based stack 34. The stack 34 may be formed by the first elastomer layer 16, the patterned conductive layer 18 and the second elastomer layer 20 and typically carries a pattern of cardiomyocytes 28 enveloped by the liquid container 26 as previously explained. These features are not explicitly shown in FIG. 3(a) for reasons of clarity only. The stack or foil 34 is typically kept very thin to optimize its stretchability.

As shown in FIG. 3(b), the device may further comprise a chamber 32' having an inlet 36. The chamber 32' is in communicative contact with the cavity 32 such that the pressure in the cavity 32 may be regulated, e.g. reduced or increased by withdrawing or adding a gas such as air via the inlet 36. This forces the stack 34 to stretch in a direction out of the plane of the substrate 10, e.g. into the cavity 32 when reducing the pressure therein or away from the cavity 32 when increasing the pressure therein. Consequently, the live cardiomyocyte cells adhered to the stack 34 are also stretched in this process. In FIG. 3(c), the autonomous contraction of the cardiomyocytes triggers an in-plane deformation of the stack 34, which comprises a thickening (contraction) of the stack 34 under the cardiomyocytes and a thinning (stretching) of the stack 32 outside the area in which the cardiomyocytes are located.

The fact that the device as demonstrated in FIG. 3(a)-(c) has a stack 34 that can be stretched has two main advantages. Firstly, repetitive stretching may be applied to immature stem cells to differentiate these stem cells into cardiomyocytes, thereby yielding a device for determining the cardiotoxicity of chemical compounds that comprises fully differentiated cardiomyocytes, which improves the relevance of the clinical data obtained with this device. Secondly, the stack 34 may be stretched in-sync with the contraction rhythm of the cardiomyocytes to resemble the beating heart. This for instance allows for the attached cardiomyocytes to be passively stretched to allow ion channel measurements in a dynamic cardiomyocyte model system mimicking the heart at rest and under controlled (patho)-physiological stress. The cardiomyocyte contraction rhythm may be autonomous or electrically induced.

The electrode arrangement in the stack 34 may take any suitable shape. In an embodiment shown in FIG. 4, the electrode arrangement comprises a circular arrangement covered by a cylindrical liquid container 26 for holding a liquid containing nutrition and/or one or more chemical compounds, i.e. pharmaceutical drugs. The container 26 envelopes a radial pattern of adhesive strips 24, e.g. fibronectin strips to which the cardiomyocytes are fixed, e.g. adhered. The radial pattern of stripes promotes the contraction of the cardiomyocytes in a radial pattern, causing a thickening of the central portion of the stack 34, as previously explained. Four stripes are shown for reasons of clarity only. The stack 34 may carry any suitable number of stripes. The pattern of electrodes 114 is aligned with these strips. The electrodes 114 are connected to bond pads 110 via connectors 112, as previously explained. The bond pads 110 may be arranged in any suitable pattern such as a rectangular or square pattern.

At this point, it is emphasized that the stretchable nature of the stack 34 does not have to be achieved by the use of elastomeric materials. Alternatively, the stack 34 may be corrugated, such that the necessary stretchability is achieved through the corrugations, as will be explained in more detail later. For such embodiments, materials other than elastomers may be used. FIG. 5 shows an example electrode arrangement of such a corrugated stack. The connections 112 from the bond pads 110 to the electrodes 114 are of a substantially linear nature and run in a direction perpendicular to the corrugations 140 in the stack. The cardiomyocyte stripes typically also run in the direction perpendicular to the corrugations 140 in the stack.

To facilitate the stretching of the stack arrangement of FIG. 5, openings 120 are provided alongside the stack. As a consequence, the liquids containing the nutrition and the chemical compounds to be tested, e.g. pharmaceutical drugs, will envelope both sides of the stack, i.e. also fill the cavity 32, resulting in a "zero" load on the stack as a result of the weight of the liquid. In this case, the out-of-plane stretching of the stack may be invoked mechanically. It is pointed out that a stack comprising the circular electrode arrangement of FIG. 4 may also comprise openings 120 to reduce the "zero" load on the stack.

In a preferred embodiment, the patterned conductive layer 18 in the elastomer-based stack comprises Ti/Au as the conductive material because it has been shown that thin titanium and gold layers can be stretched up to 100%, thus allowing the conductive pattern to be stretched without damage. Alternatively, TiN or another suitable stretchable conductor may be considered.

FIG. 6 schematically depicts a method of manufacturing a device according to FIG. 3 in which the stack 34 is elastomer-based. In step (a), a silicon substrate 10 having a thickness of around 300-400 micron is supplied and its back side is provided with a suitable hard-etch mask 50, e.g. LPCVD grown silicon nitride ($Si_3N_4$). The etch mask 50 is patterned to define the cavity to be formed in the substrate 10. In other words, the etch mask pattern defines the position and size of the stretchable area.

In next step (b), a dielectric layer 12, e.g. a thermal oxide layer, is grown on the front side of the substrate 10 to a thickness in the region of 1 micron or less, e.g. 0.5 micron. This is followed by the deposition and patterning of a first elastomer layer 16, e.g. a first layer of PDMS, as shown in step (c). This layer may be deposited in any suitable manner, such as by spin-coating. PDMS is a particularly suitable material because it is bio-compatible and can be elongated up to 100%.

In step (d), a patterned conductive layer 18 is formed over the first elastomer layer 16. This may be achieved in any suitable way. For instance, a Ti/Au stack or TiN may be used as a conductive material, and may be sputter-coated and patterned to form the electrode and interconnection pattern, such as the pattern shown in FIG. 4. Note that the first elastomer 16 has been patterned such that the elastomer is absent underneath the bond pads to allow for reliable wire-bonding.

The elastomer-based stack is completed in step (e), in which a second elastomer layer 20, such as a second layer of PDMS is deposited in any suitable manner to seal the interconnect patterns 112 and patterned to expose the electrodes 114 and bondpads 110 shown in e.g. FIG. 4.

Next, the cavity in the substrate 10 is formed, as shown in step (f) by wet-etching the exposed back side of the substrate 10 with any suitable etchant, of which a $HF/HNO_3$/acetic acid (HNA) etchant is a non-limiting example (FIG. 6(f)). After removal of the hard-etch mask in step (g), the substrate 10, which typically is a wafer carrying multiple sensor devices, is diced in step (h), thereby separating the individual sensor devices. In case the dielectric layer 12 has not yet been fully removed by the wet-etching step, a further wet etching step may be applied to remove residual dielectric layer material. Finally, the container 26 is glued to the front side of the device in step (i). The adhesive layer pattern for adhering the cardiomyocytes to the elastomer-based stack, e.g. a fibronectin pattern, may be applied inside the container 26, e.g. by stamping, after which the cardiomyocytes are applied to this adhesive pattern. This is preferably done immediately prior to use of the device to ensure that the cardiomyocytes are 'fresh' when being used.

FIG. 6(j) depicts an embodiment of the interconnections 112 between the bond pads 110 and the electrodes 114 of the conductive layer 18. The interconnections 112 have been designed in a meandering shape to further facilitate the stretching of the elastomer-based stack.

FIG. 7 shows a first embodiment of a method to form a device having a stack that can be deformed by virtue of the stack comprising corrugations, as previously discussed in the description of FIG. 6. In step (a), a silicon substrate 10 having a thickness of around 300-400 micron is supplied and its back side is provided with a suitable hard-etch mask 50, e.g. LPCVD grown silicon nitride ($Si_3N_4$). The etch mask 50 is patterned to define the cavity to be formed in the substrate 10. This step is substantially identical to step (a) in FIG. 6. Next, as shown in step (b), corrugations 10' are formed in substrate 10 in any suitable manner, e.g. by milling or etching. It is noted that although the corrugations are shown to have a triangular shape as a non-limiting example only. Preferably, the corrugation profile has a more rounded or wavy shape. How such a wavy corrugated pattern can be achieved will be discussed in more detail later.

In step (c), a thermal oxide etch stop layer is grown, followed by the deposition of a conformal first layer 16 in step (d). The conformal material may be any suitable material. A preferred candidate material is parylene because it is a biocompatible material with an exceptional step-coverage that can be CVD deposited at a room temperature. At the location of the bond pads, openings are etched in the layer 16.

In step (e), the patterned conductive layer 18 is formed, e.g. a TiN layer is sputter-coated and patterned, to form the electrode and interconnection pattern. A second elastomeric layer 20, e.g. a second parylene layer is deposited to seal the interconnections 112 and patterned to expose the electrodes 114 and the bond pads 110, as shown in step (f).

In step (g), the cavity 32 is formed underneath the stretchable area by wet-etching the exposed back side of the substrate with HNA. An additional wet etching step may be applied to remove any residual thermal oxide etch stop if necessary. After removal of the hard-etch mask 50 in step (h), the individual devices are separated by dicing the substrate wafer in step (i), after which the container 26 is adhered to the front side of the substrate 10 in step (j). The adhesive layer pattern for adhering to the cardiomyocytes to the stretchable area, e.g. a fibronectin pattern, may be applied inside the container 26, e.g. by stamping, after which the cardiomyocytes are applied to this adhesive pattern.

It is reiterated that it is preferable to provide the substrate 10 with corrugations 10' having a rounded or wavy shape. One of the reasons for this is that the subsequent layers to be formed over the corrugations, such as the elastomer layers 16 and 20, can be more easily formed due to the fact that there is a reduced risk of disruptions in the continuity of these layers, which may occur in the sharp corners at the bottom of triangularly shaped corrugations due to the difficulty of properly lining these corners with such subsequent layers.

FIG. 8 shows a first embodiment of a method to form rounded corrugations 10', which utilizes the etching behavior of silicon when exposed to an isotropic wet etching step. In step (a), the silicon substrate 10 is provided with a suitable patterned hard mask 50', with the pattern reflecting the desired locations of the recesses of the corrugations 10'. A suitable hard-etch mask such as an LPCVD grown $Si_3N_4$ layer may be used.

In step (b), the exposed parts of the front side of the substrate 10 are exposed to an isotropic wet etch mixture such as HNA or a $HF/HNO_3/H_2O$ mixture. The isotropic etching step results in an under-etch which laterally extends to approximately 0.7 times the etch depth. Alternatively, a dry etch may be applied, such as a $CF_4/O_2$ plasma. Finally, the hard etch-mask 50' is removed in step (c). This yield a corrugation pattern in which the 'valleys' 10' in the substrate 10 are rounded, whereas the 'peaks' separating neighboring 'valleys' are flat.

In a second embodiment, these 'peaks' are also rounded, such that a more wave-like, i.e. wavy corrugation pattern is achieved. This is shown in FIG. 9. In step (a), an oxide layer 12' is grown over the substrate 10 prior to the deposition of the hard-etch mask 50'. The oxide layer 12' and hard-etch mask 50' are patterned to expose the regions of the substrate 10 in which the corrugation 'valleys' 10' are to be etched.

Next, as shown in step (b), the silicon substrate 10 is isotropically etched to an intermediate depth, which is less than the finally required depth. This etch does not affect the hard-etch mask 50', e.g. $Si_3N_4$ mask 50', and only slightly affects the oxide layer 12'. In a subsequent etching step (c), the oxide 12' underneath the hard-mask layer 50' is etched, for instance by means buffered oxide etch consisting of a mixture of $NH_4F/HF$. It is noted that a certain amount of "over-etch" will be required.

Next, the silicon is again isotropically etched in etching step (d). Since the isotropic etch preferentially attacks sharp silicon corners, this step will result in a wavy silicon pattern. After removal of the hard mask 50' and residual oxide layer 12' in step (e), the device manufacture can continue as outlined in FIG. 7 and its detailed description. The wavy pattern can be optimized by adjusting the pitch between the patterns and the thickness of the oxide layer 12'.

A "wavy" corrugated structure with a finer pitch may be obtained by using LOCOS, as shown in FIG. 10. This will be briefly described only because LOCOS techniques are well known to the person skilled in the art. In step (a), a silicon substrate 10 is provided carrying a suitable LOCOS stack consisting of a pad oxide 12' and an LPCVD deposited $Si_3N_4$ hard mask layer 50'. This stack is patterned to expose the regions of the substrate 10 in which the corrugations 10' are to be formed. In step (b), the exposed regions of the silicon substrate are thermally oxidized to form the thermal oxide layer 52. The $Si_3N_4$ hard mask layer 50' will not be oxidized; however at the edges of the $Si_3N_4$ hard mask layer 50' the thermal oxide layer 52 will extend underneath the nitride, i.e. form the well-known birds-beaks associated with LOCOS oxidation.

The size and the shape of the birds-beak are determined by the thicknesses of the pad-oxide layer 12', the $Si_3N_4$ hard mask layer 50' and the oxidizing conditions. By optimizing these conditions and the pitch between the waves, a corrugated structure will be obtained after removal of the $Si_3N_4$ hard mask layer 50' in step (c) and oxide removal in step (d).

Alternatively, the corrugated silicon pattern may be obtained using gray-scale lithography or using resist flow.

It is should be mentioned that the fibronectin, or any other suitable adhesive, can be applied by stamp printing, spray coating in combination with photo-lithography. In a preferred embodiment, the fibronectin is applied by ink-jet printing. The adhesive fibronectin pattern preferably is applied after placement of the container on the stretchable stack, after which the cardiomyocytes are applied to this adhesive pattern.

It is further pointed out that the electrode array may be supplemented with a plurality of sensors other than electrodes. Non-limiting examples of such sensors include strain-gauges that can measure the amount of force induced by the contraction of the cardiomyocytes, and micro-calorimeters that can measure the amount of heat produced by these cells.

Finally, it should be pointed out that although the embodiments of the device of the present invention have been shown to comprise passive devices only in the patterned conductive layer 18, the electrode array formed therein may alternatively contain active devices for forming circuits that for example can perform the function of signal amplification and signal shaping.

It should be appreciated that the device of the present invention makes it possible to measure the cardiomyocyte ion channel activity to detect QT elongation, i.e. the elongation of the interval representing the duration of ventricular depolarization and subsequent repolarization, measured from the beginning of the QRS complex to the end of the T wave of the heart rhythm, as well as other electrophysio logical abnormalities in the heart cell.

Compared to electrophysiological measurements performed in a steady state system, where the effect of passive cardiomyocyte stretch due to filling of the left ventricle during diastole are not taken into account, the device of the present invention can be used to develop a heart cell model which is capable of accurately simulating a large variety of arrhythmias, such as arrhythmias due to long QT syndrome that occur during physical exertion, or pathophysiological conditions associated with increased cardiac output (like fever, anemia), when both heart rate, end-diastolic ventricular volume and filling pressure increase to induce the required increase in cardiac output.

The direct relationship between the level of stretch of the ventricular wall cardiomyocytes and the contraction force of the cardiomyocytes is described in the Frank-Starling law. With increased stretch, contraction force increases until a point is reached where further stretch induces a reduction in cardiac output. This has been described as electromechanical feedback. This (patho)physiological stretching of the cardiomyocytes plays a role in ion channel activity and proneness to arrhythmias. The stretchable device of the present invention makes it possible to measure ion channel activity under controlled (patho-)physiological conditions of cardiomyocyte stretch and contraction.

Such measurements of ion channel activity as described above can be performed in specific cardiac disease models, such as a disease model for hypertrophic cardiomyopathy and heart failure. Prolonged excessive stretching (associated with increased cardiac load) of the cardiomyocytes in the cardiac ventricular wall leads to hypertrophy, potentially resulting in heart failure. Longer periods of controlled stretch-contraction cycles applied to the cardiomyocytes which are adhered to the stretchable stack of the device of the present invention, with excessive passive stretch applied, are expected to induce cardiomyocyte hypertrophy and to simulate heart failure, and continuous recording of ion channel activity and contraction force may reveal information on the underlying pathogenetic mechanism. The above-described model system for hypertrophic cardiomyopathy can be used for drug target discovery, i.e. the identification of specific drug target molecules that play a causative role in the disease process and the discovery of compounds that can be used to treat the disease, as well as for drug development. Obviously, the cardiotoxicity of chemical compounds may also be tested in these disease states.

The aforementioned disease models may be implemented by exposure of the live cardiomyocyte cells to solutions that comprise solutes present in the blood such as electrolytes, $O_2$, $CO_2$, glucose and so on in concentrations that are indicative of the simulated disease. Hence, the response of the cardiomyocytes to such solutes can be used to gain a better understanding of the effect of the simulated disease on these cells.

The method for developing a disease model for a disease that is caused by or modified by stretching of cells, comprises the steps of:

Attaching at least one cell to an adhesive surface pattern (24)

Stretching the at least one cell by an externally applied force

Measuring an action potential of the at least one cell electrically and/or optically, the action potential being monitored and/or interpreted over time.

To develop and build the disease model for drug target discovery and drug development and drug toxicity measurement, several experimental steps are performed:

1. The required viable cells, that represent the diseased tissue are produced/cultured, according to existing protocols. They can be obtained directly from cell lines, or from an animal or human tissue source and prepared for culturing. They can also be obtained from animal or human stem cells that have been induced to differentiate to the required cell type (s).

2. On the surface of the device as described above, a fibronectin or other extracellular matrix or other adhesive layer may be deposited or printed in order for the cells to attach to the surface and stay viable.

3. The requried number of cells (depending on the surface area and cell type) may be plated on the substrate as described above, and maintained in a healthy viable condition in the right culture medium, to measure certain cell-specific variables, like ion channel activity or electric action potential.

4. Sometimes an additional or repeated action(s)/procedure(s) may be required to further develop the disease model, sometimes this may entail either one-time, continuous, or repeated stretching of the cells, to 100-200% or more of their original length, either in plane or in such a way (usually) that they stretch out of plane, mimicking the required disease situation. Sometimes there are shorter or longer cycles of stretching followed by a defined period of relaxation. During this process the action potential of the cells is measured, and interpretated with respect to the activity of the one or more membrane ion channels involved in generating ion fluxes that generate electrical potential changes.

5. One or more disease-specific variables are measured to prove that the disease model resembles the actual disease to such extent that it can be used for purposes of drug target discovery, drug development and drug toxicity.

6. For purpose of drug target discovery, drug development or drug toxicity the cells will be stretched in the same ways as described under (4), in such a way that the stretch occurs either in or (mostly) out of plane and the action potential is continuously monitored and interpreted. During this procedure chemical or biological compounds can be added that need to be investigated.

7. After finishing the stretching part of the experiment, several other measurements can be performed on the cells, like DNA/RNA/protein/metabolyte analysis, to investigate the action of the added compounds or other change in the cell environment, like a pH or electrolyte, glucose, oxigen or nutritional supplement or metabolite concentration change, on the function/activity/viability of the cells.

Disease models that can in this way be created can be divided in several categories, dependent on:

the percentage of stretch required, this is determined either by the physiological stretching that occurs in vivo. For example during heart beating when cardiomyocytes and endothelial cells are stretched to a physiologically level, dependent on the cardiac output/blood pressure with every beat; or pathophysiological stretching like for example occurs in a tumor or intracerebral bleeding or subdural hematome.

the level to which the stretch takes place out-of-plane. For example for a model to simulate a beating heart the cardiomyocyte cell layer must be pushed out-of-plane during the stretch, and returned in plane during the relaxation part of the heart beat. If the model for example mimicks heart failure, the cardiomyocytes are more extensively stretched out of plane to simulate increased filling of the heart ventricle with blood, over the top in the Frank-Starling curve. For stretch in a model for a growing tumor, the stretch will be increasingly out of plane.

The manner in which the stretch is applied with time: one-time short, continuous for longer period of time, or repeated. In a cardiac or endothelial model the stretch is applied repeatedly. For example, in a tumor model the stretch is continuous and increasing. For example, in a model for intracerebral bleeding the stretch is short and rapidly increasing to high/maximum level.

the time period during which the stretch is applied: for example intermittent (stretch-contraction cycles) with the frequency of a heart beat under different conditions; or with the stretch slowly increasing over hours in the case of a model for subdural hematoma in the brain; rapid increase in stretch within hours in the case of a model for intracerebral bleeding, very slow in case of a model for a brain tumor)

the type of adhesion between the individual cells. The extent to which stretching decreases the adhesion between cells depends on the strength of the adhesive molecular bonds and the cellular processes that regulate these bonds. For example in case of a model for cancer, the level of stretch required to simulate certain pathogenetic changes in the cancer cells will be tuned to the strength of the intercellular adhesions, which is likely to be specific for different tumors, such that the electrical resistance over the cell layer is decreased.

The method for developing disease models as described above is very suitable for those diseases that are caused by or modified by stretching of cells, resulting in abnormal action potential or functioning of ion channels. Examples are endothelial diseases like atherosclerosis and hypertension and migraine; neurological diseases like whiplash, concussion, brain tumors, intracerebral bleeding and subdural hematoma; muscle diseases like Duchenne, and gastrointestinal disease like irritable bowel syndrome.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

The invention claimed is:

1. A device for determining the cardiotoxicity of a chemical compound comprising:
   a substrate (10) carrying a deformable stack (34), said stack being partially detached from the substrate by a cavity (32) allowing an out-of-plane deformation of the stack, said stack comprising a first deformable layer (16), a second deformable layer (20) and a multi-electrode structure (18) sandwiched between the first and second deformable layers, the second deformable layer carrying a pattern of cardiomyocytes (28) adhered thereto; and
   a liquid container (26) mounted on the substrate for exposing the cardiomyocytes to the chemical compound.

2. The device of claim 1, wherein one end of the deformable stack (34) is detached from the substrate (10) to facilitate the out-of-plane deformation of the stack upon contraction of the cardiomyocytes (28).

3. The device of claim 1, wherein:
the cavity (32) is formed in the substrate (10);
the stack (34) extends over the cavity, and
opposite ends of the stack are attached to the substrate (10), thereby facilitating the out-of-plane deformation of the stack (34) by an externally applied force.

4. The device of claim 3, further comprising an inlet (36, 120) for filling the cavity (32) with a fluid.

5. The device of claim 4, wherein the stack (34) comprises the inlet (120).

6. The device of claim 3, wherein the pattern of cardiomyocytes (28) is a radial pattern.

7. The device of claim 3, wherein the stack (34) is corrugated.

8. The device according to claim 1, wherein the out-of-plane deformation of the stack (34) is larger than 30%.

9. A method of manufacturing a device according to claim 1, comprising:
growing an oxide layer (12) on the substrate (10);
depositing the first deformable layer (16) over the oxide layer;
depositing and patterning a conductive layer (18) over the first deformable layer, thereby forming the multi-electrode structure;
depositing a second deformable layer (20) over the first deformable layer;
patterning the second deformable layer to provide access to the multi-electrode structure;
depositing an adhesive pattern (24) over the patterned second deformable layer;
adhering cardiomyocytes (28) to the adhesive pattern;
adhering the liquid container (26) to the second deformable layer; and
forming the cavity (32) underneath the first deformable layer.

10. The method of claim 9, in which the steps of depositing an adhesive pattern (24) over the patterned second deformable layer and adhering cardiomyocytes (28) to the adhesive pattern are performed after forming the cavity (32) underneath the first deformable layer.

11. The method of claim 10, wherein forming said cavity (32) comprises:
depositing a sacrificial layer (14) over the oxide layer (12) prior to the deposition of the first deformable layer (16), said sacrificial layer defining the cavity volume; and
removing the sacrificial layer after the deposition of the second deformable layer (20).

12. The method of claim 10, wherein forming said cavity (32) comprises:
growing a mask (50) on the back side of the substrate (10);
patterning said mask to define the cavity area;
etching the back side of the substrate to expose the first deformable layer (14); and
removing the patterned mask from the backside of the substrate.

13. The method of claim 12, further comprising forming a corrugated pattern (10') in the substrate (10) prior to forming the oxide layer (12).

14. The method of claim 13, wherein forming said corrugated pattern comprises:
depositing a silicon oxide layer (12') over the substrate (10);
depositing a silicon nitride layer (50') over the silicon oxide layer;
patterning the silicon oxide layer and silicon nitride layer, thereby exposing selected parts of the substrate;
exposing said selected parts to a series of etching steps to form said corrugated pattern; and
removing the silicon oxide layer and silicon nitride layer.

15. The method of claim 13, wherein said corrugated pattern is formed by a LOCOS oxidation step followed by an etching step in which the LOCOS oxide is removed.

16. A method of determining the cardiotoxicity of a chemical compound, comprising:
providing the device of claim 1;
filling the container (26) with a medium comprising the chemical compound to expose the cardiomyocytes (28) to said compound; and
measuring the response of the cardiomyocytes to said exposure.

17. A method of using the device according to claim 1 for drug target discovery and/or drug development, comprising:
providing the device of claim 1;
filling the container (26) with a medium comprising the chemical compound to expose the cardiomyocytes (28) to said chemical compound; and
measuring the response of the cardiomyocytes to said exposure.

* * * * *